(12) United States Patent
Tsuji et al.

(10) Patent No.: US 6,878,138 B2
(45) Date of Patent: Apr. 12, 2005

(54) DISPOSABLE LIQUID-ABSORBENT PAD

(75) Inventors: Tomoko Tsuji, Kagawa-ken (JP); Takako Uosawa, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 348 days.

(21) Appl. No.: 10/147,640

(22) Filed: May 17, 2002

(65) Prior Publication Data

US 2002/0173763 A1 Nov. 21, 2002

(30) Foreign Application Priority Data

May 21, 2001 (JP) ........................................ 2001-151447

(51) Int. Cl.[7] .............................................. A61F 13/15
(52) U.S. Cl. ............................ 604/385.09; 604/385.19; 604/385.201
(58) Field of Search ....................... 604/385.24–385.28, 604/385.04, 385.09, 385.19, 385.101, 385.201

(56) References Cited

U.S. PATENT DOCUMENTS

| | | | | |
|---|---|---|---|---|
| 4,067,336 A | | 1/1978 | Johnson | |
| 4,182,334 A | * | 1/1980 | Johnson | 604/385.201 |
| 4,505,706 A | | 3/1985 | Erpicum et al. | |
| 4,560,380 A | * | 12/1985 | Tharel | 604/385.19 |
| 4,731,070 A | * | 3/1988 | Koci | 604/385.201 |
| 5,380,310 A | | 1/1995 | Mitrani | |
| 6,471,681 B1 | * | 10/2002 | Ronnberg et al. | 604/385.19 |
| 6,592,562 B2 | * | 7/2003 | Menard et al. | 604/385.04 |

FOREIGN PATENT DOCUMENTS

| | | |
|---|---|---|
| EP | 0558070 | 9/1993 |
| JP | A 6-21621 | 3/1994 |

* cited by examiner

Primary Examiner—Larry I. Schwartz
Assistant Examiner—C. Lynne Anderson
(74) Attorney, Agent, or Firm—Butzel Long (57) ABSTRACT

A disposable liquid-absorbent pad includes a liquid-pervious topsheet, a liquid-impervious backsheet and a liquid-absorbent core interposed between these two sheets. The pad is folded inwardly in the vicinity of transversely opposite side edges with the topsheet inside in a rear region, and folded outwardly in a transverse direction along folding lines extending in a longitudinal direction and joined together along the folding lines so that in the rear region of the pad defines an excretion receiving space extending up- and rearward to a rear end defining an apex and a pair of flanges extending outwardly from the respective folding lines to the side edges.

3 Claims, 9 Drawing Sheets

DISPOSABLE LIQUID-ABSORBENT PAD

BACKGROUND OF THE INVENTION

This invention relates to a disposable liquid-absorbent pad for absorption and containment of excretion discharged thereon.

Japanese Utility Model Application No. 1994-21621A discloses a disposable pants-type underwear having a waist-hole and a pair of leg-holes and a liquid-absorbent pad folded in U-shape and attached to an inner side of its crotch region. This liquid-absorbent pad comprises a liquid-pervious topsheet, a liquid-impervious backsheet and a liquid-absorbent core interposed between these sheets and contoured by transversely opposite side edges extending in U-shape and front and rear ends extending in a waist-surrounding direction. The liquid-absorbent core is bonded in the vicinity of the front and rear ends to the inner side of the pants. With the pants disclosed in this Publication, it is claimed that excretion discharged thereon can be effectively absorbed and retained by the liquid-absorbent pad without any anxiety of leakage of excretion from the crotch region.

However, the pad disclosed in the above-cited Publication is substantially flat and provided along its side edges as well as along its front and rear ends with no means functioning as barriers against excretion. Therefore it is apprehended that excretion might leak beyond the side edges and/or the front and rear ends if excretion spreads over the topsheet before absorbed by the core.

SUMMARY OF THE INVENTION

It is an object of this invention to provide a liquid-absorbent pad improved so as to eliminate the anxiety that excretion might leak beyond the side edges and/or the front and rear ends of the pad.

According to this invention, there is provided a disposable liquid-absorbent pad which is relatively long in dimension in a wearer's front and rear direction, comprising a liquid-pervious topsheet facing a wearer's skin, a liquid-impervious backsheet facing away from the wearer's skin and a liquid-absorbent core interposed between these sheets, the pad having, in a longitudinal direction, of a front region, a rear region and an intermediate region extending between these front and rear regions wherein the pad is contoured by transversely opposite side edges extending in the longitudinal direction, a front end extending in the front region in a transverse direction and a rear end extending in the rear region in the transverse direction.

The pad is folded inwardly in the rear region in a vicinity of transversely opposite side edges with the topsheet inside, further folded outwardly in a transverse direction along a pair of first folding lines extending inside the side edges in the longitudinal direction and joined together along the first folding lines, and the pad defines in the rear region an excretion receiving space extending up- and rearward to the rear end defining an apex and a pair of flanges extending outwardly from the folding lines to the side edges in the transverse direction.

This invention includes the following embodiments, the pad is in the rear region provided in the vicinity of the side edges with elastically stretchable members extending in the longitudinal direction bonded thereto in a stretched state.

The pad is in the front region folded inwardly with the topsheet inside in the vicinity of transversely opposite side edges, and folded outwardly in the transverse direction along a pair of second folding lines extending inside the side edges in the longitudinal direction and joined together along the second folding lines, and the pad defines in the front region a penis receiving space extending up- and forwardly to the front end defining an apex and a pair of flanges extending outward from the folding lines to the side edges in the transverse direction and the intermediate region defines, in the vicinity of the side edges, a pair of barriers extending upwardly to apices defined by the side edges.

The elastically stretchable members extending in the longitudinal direction are secured in a stretched state to the front region and the intermediate region, at least to the front region, in the vicinity of the side edges.

DETAILED DESCRIPTION OF THE PREFERRED EMBODIMENTS

Details of a liquid-absorbent pad according to this invention will be more fully understood from the description given hereunder in reference to the accompanying drawings.

Figure 1:
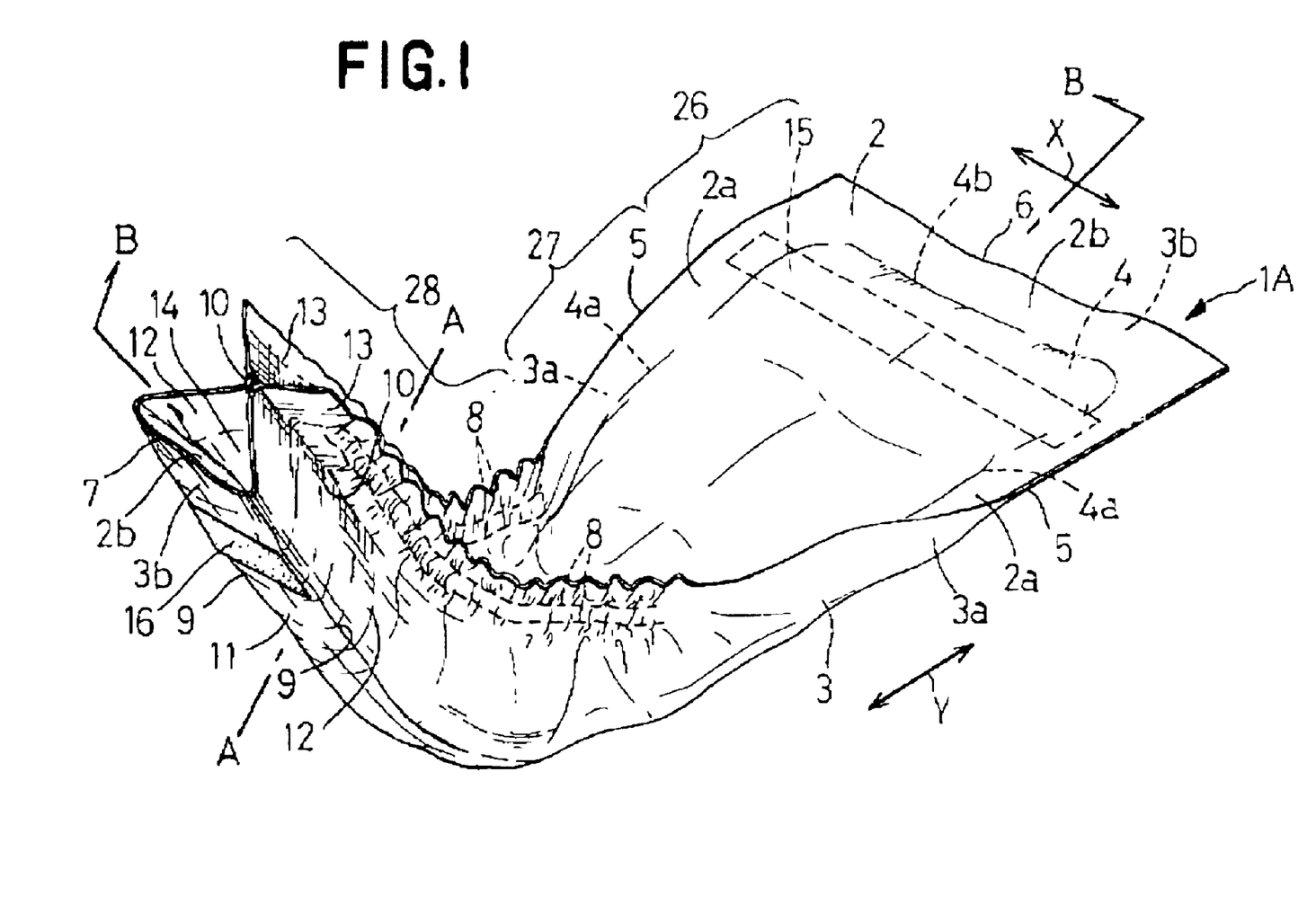
FIG. 1 is a perspective view showing a liquid-absorbent pad according to this invention.
Figure 2:
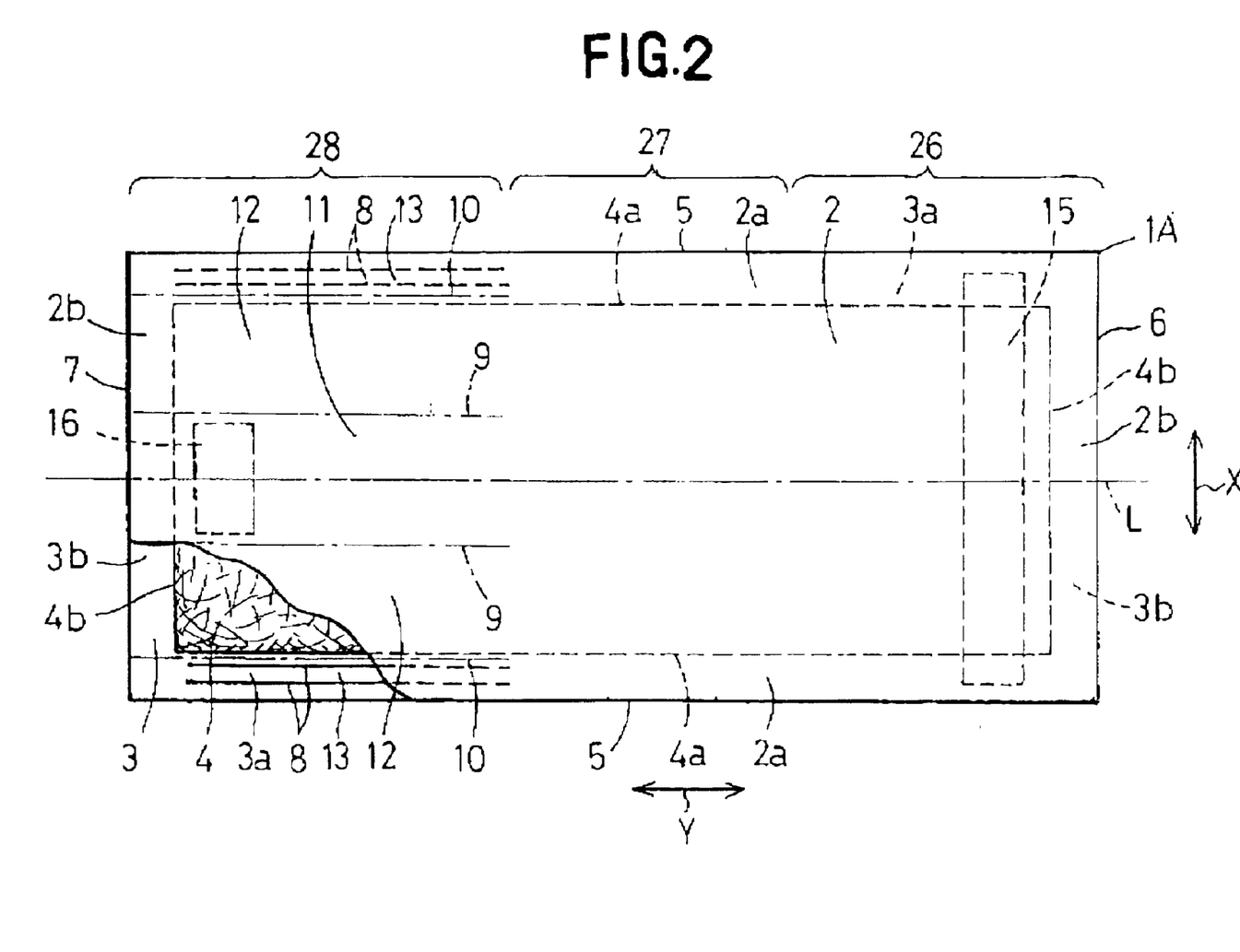
FIG. 2 is a partially cutaway plan view showing the pad before shaped into the pad.
Figure 3:
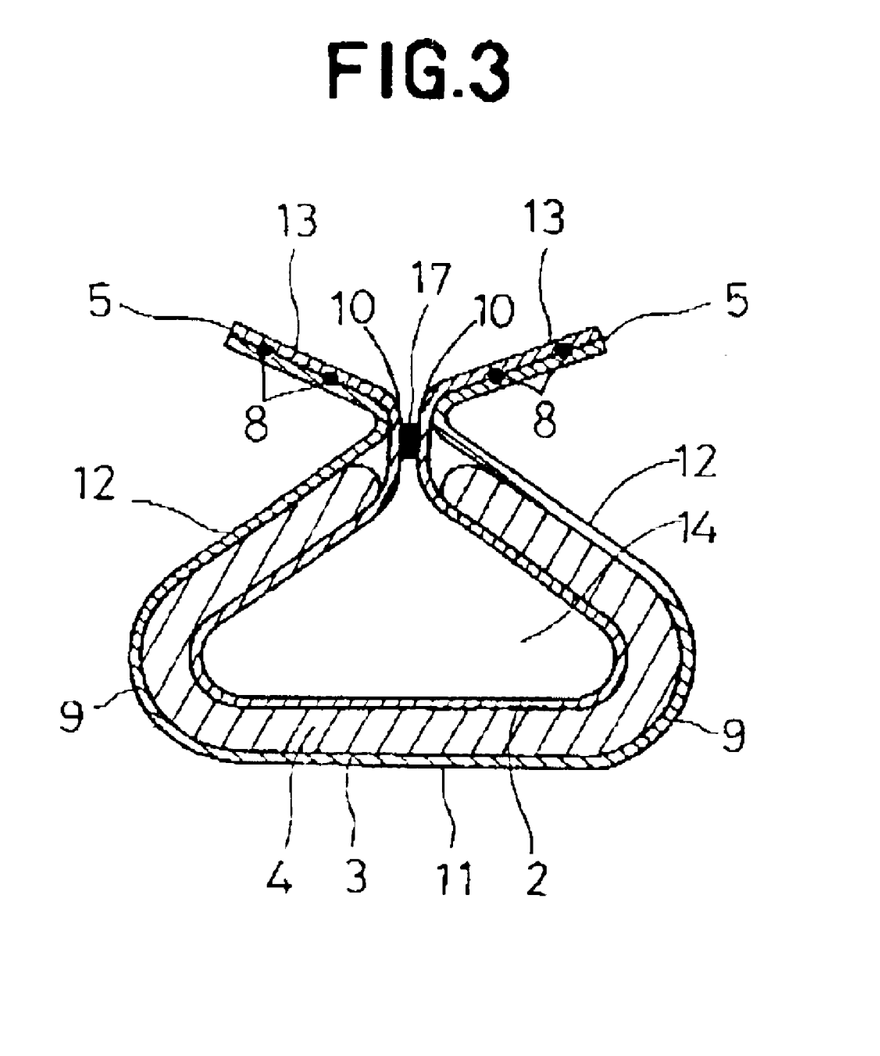
FIG. 3 is a cross-sectional view taken along a line A—A in FIG. 1.
Figure 4:
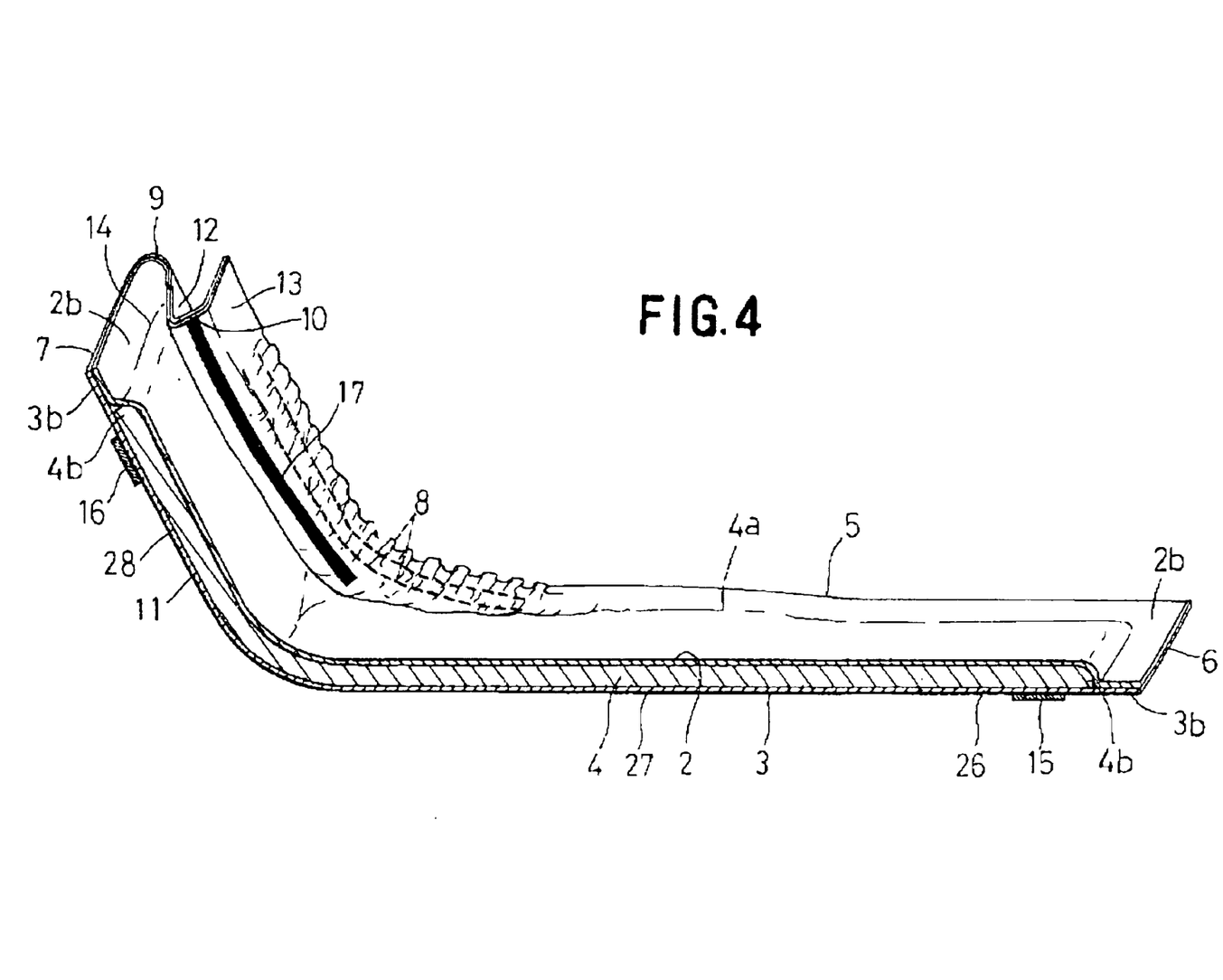
FIG. 4 is a cross-sectional view taken along a line B—B in FIG. 1.

FIG. 1 is a perspective view showing a liquid-absorbent pad 1A according to this invention, FIG. 2 is a partially cutaway plan view showing the pad 1A before shaped into the pad 1A, FIG. 3 is a cross-sectional view taken along a line A—A in FIG. 1, and FIG. 4 is a cross-sectional view taken along a line B—B in FIG. 1. In FIGS. 1 and 2, a transverse direction of the pad 1A is indicated by an arrow X and a longitudinal direction of the pad 1A is indicated by an arrow Y Expression "inner surfaces" of a liquid-pervious topsheet 2 and a liquid-impervious backsheet 3 should be understood to he the surfaces facing respectively a core 4 and expression "outer surfaces" of these sheets 2, 3 should be understood to be the surfaces facing respectively away from the core 4.

The pad 1A comprises the liquid-pervious topsheet 2 facing a wearer's skin, the liquid-impervious backsheet 3 facing away from the wearer's skin and the liquid-absorbent core 4 interposed between these sheets 2, 3. From another aspect, the pad 1A is composed, in the longitudinal direction, of a front region 26, a rear region 28 and an intermediate region 27 extending between these front and rear regions 26, 28. The pad 1A is contoured by transversely opposite side edges 5 extending in the longitudinal direction, a front end 6 extending in the transverse direction in the front region and a rear end 7 extending in the transverse direction in the rear region 28.

In the pad 1A, respective lateral portions 2a, 3a of the top- and backsheets 2, 3 extending outwardly beyond transversely opposite side edges 4a of the core 4 in the transverse direction are overlaid and bonded to each other. Similarly, respective end portions 2b, 3b of the top- and backsheets 2, 3 extending outwardly from longitudinally opposite ends 4b of the core 4 are overlaid and joined to each other. The core 4 is joined to the inner surface of the topsheet 2 and/or the backsheet 3.

The rear region 28 of the pad 1A is provided in the vicinity of the side edges 5 with a plurality of elastically stretchable members 8 extending in the longitudinal direction and secured in a stretched state thereto. These elastic members 8 are interposed between the top- and backsheets 2, 3 and secured to the respective inner surfaces of these sheets 2, 3.

In the rear region 28, the pad 1A is folded inwardly to the transverse direction with the topsheet 2 inside along a pair of inwardly folding lines 9 extending in the longitudinal direction on both sides of a longitudinal center line L (See FIG. 2) which is bisecting the distance between the opposite side edges 5. In the rear region 28, the pad 1A is further folded outwardly to the transverse direction along a pair of outward folding lines 10 (first folding lines) extending in the longitudinal direction between the respective inward folding lines 9 and their respective adjacent side edges 5 In the rear region, the pad 1A is folded and overlaid along the outward folding lines 10 in the vicinity of the side edges 5 and the outer surface of the topsheet 2 is bonded together along these outward folding lines 10 by means of hot melt adhesive 17.

The pad 1A folded in this manner in the rear region 28 defines a bottom wall 11 extending between the inward folding lines 9, opposite side walls 12 extending between the respective inward folding lines 9 and their respectively adjacent outward folding lines 10, and a pair of flanges 13 extending outwardly in the transverse direction from the respective outward folding lines 10 toward their respectively adjacent side edges 5. In this manner, the pad 1A defines in the rear region 28 an excretion receiving space 14 surrounded by the bottom wall 11 and the opposite side walls 12. The excretion receiving space 14 has an apex defined by the rear end 7 and uprises obliquely rearward In the front region 26, the outer surface of the backsheet 3 is coated an self-adhesive 15 protectively covered with release paper (not shown). Also in the bottom wall 11, the outer surface of the backsheet 3 is coated with an adhesive 16 protectively covered with release paper (not shown).

To obtain the pad 1A of FIG. 1 from a state shown in FIG. 2, the pad 1A is folded in the rear region 28 along the inward folding lines 9 with the topsheet 2 inside, then folded along the outward folding lines 10 and finally the outer surface of the tosheet 2 is joined together along the outward folding lines 10.

Figure 5:
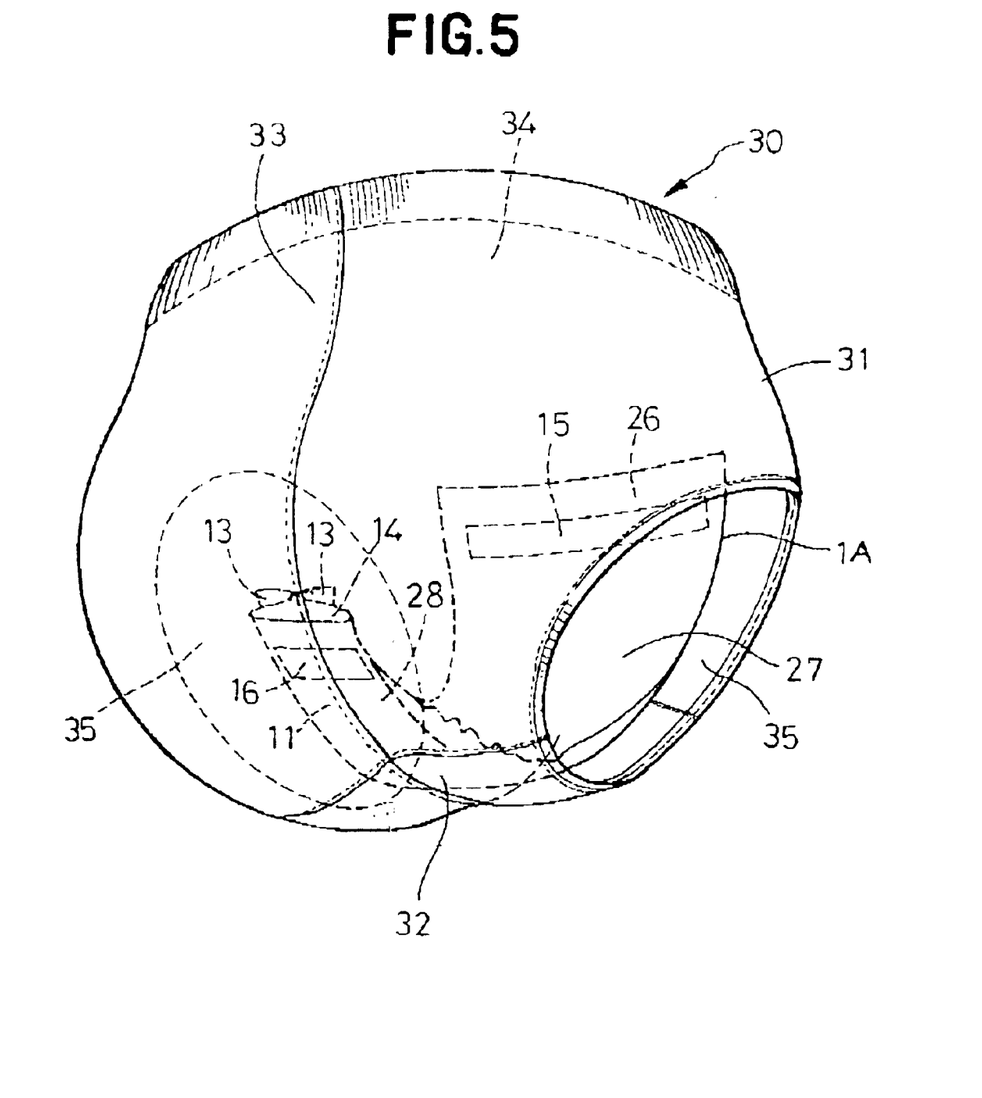
FIG. 5 is a perspective view showing the pad of FIG. 1 as attached to the inner side of the pants.

FIG. 5 is a perspective view showing the pad 1A of FIG. 1 as attached to the inner side of a pair of pants 30. The outer surface of the backsheet 3 of the pad 1A is joined to the inner side of the pants 30 by means of adhesives 15, 16. The pants 30 are composed of a front waist region 31, a rear waist region 33 and a crotch region 32 extending between these waist regions 31, 33 so as to define a waist-hole 34 and a pair of leg-holes 35. In the pants 30, the pad 1A extends across the crotch region 32 into the front and rear waist regions 31, 33. In the pants 30, the front region 26 of the pad 1A corresponds to the front waist region 31, the rear region 28 of the pad 1A corresponds to the rear waist region 33 and the intermediate region 27 corresponds to the crotch region 32.

The rear region 28 of the pad 1A covers substantially a middle zone of the wearer's hip with the flanges 13 defined in this rear region 28 come in contact with the wearer's hip when the pants 30 are worn by the wearer. The pad 1A has the excretion receiving space 14 extending up- and rearward toward its apex defined by the rear end 7 and therefore it is unnecessary to bend the rear region 28 along the curvature of the pants 30 when the pad 1A is attached to the pants 30. This feature facilitates the pad 1A to be attached to the pants 30.

The excretion receiving space 14 defined by the rear region 28 of the pad 1A can prevent leakage of excretion beyond the side edges 5 and the rear end 7 in the rear region 28 of the pad 1A. In addition, as the pad 1A comes in contact with the wearer's hip through the flanges 13, thereby protecting the wearer from experiencing an uncomfortable irritation by the side edges 5 which otherwise might directly contact the wearer's hip.

In the pad 1A, the elastic member 8 attached to the pad 1A in the vicinity of the side edges 5 in the rear region 28 facilitate the excretion receiving space 14 to uprise. It is not essential to provide the pad 1A with the elastic members 8 in the vicinity of the side edges 5 in the rear region 28.

Figure 6:
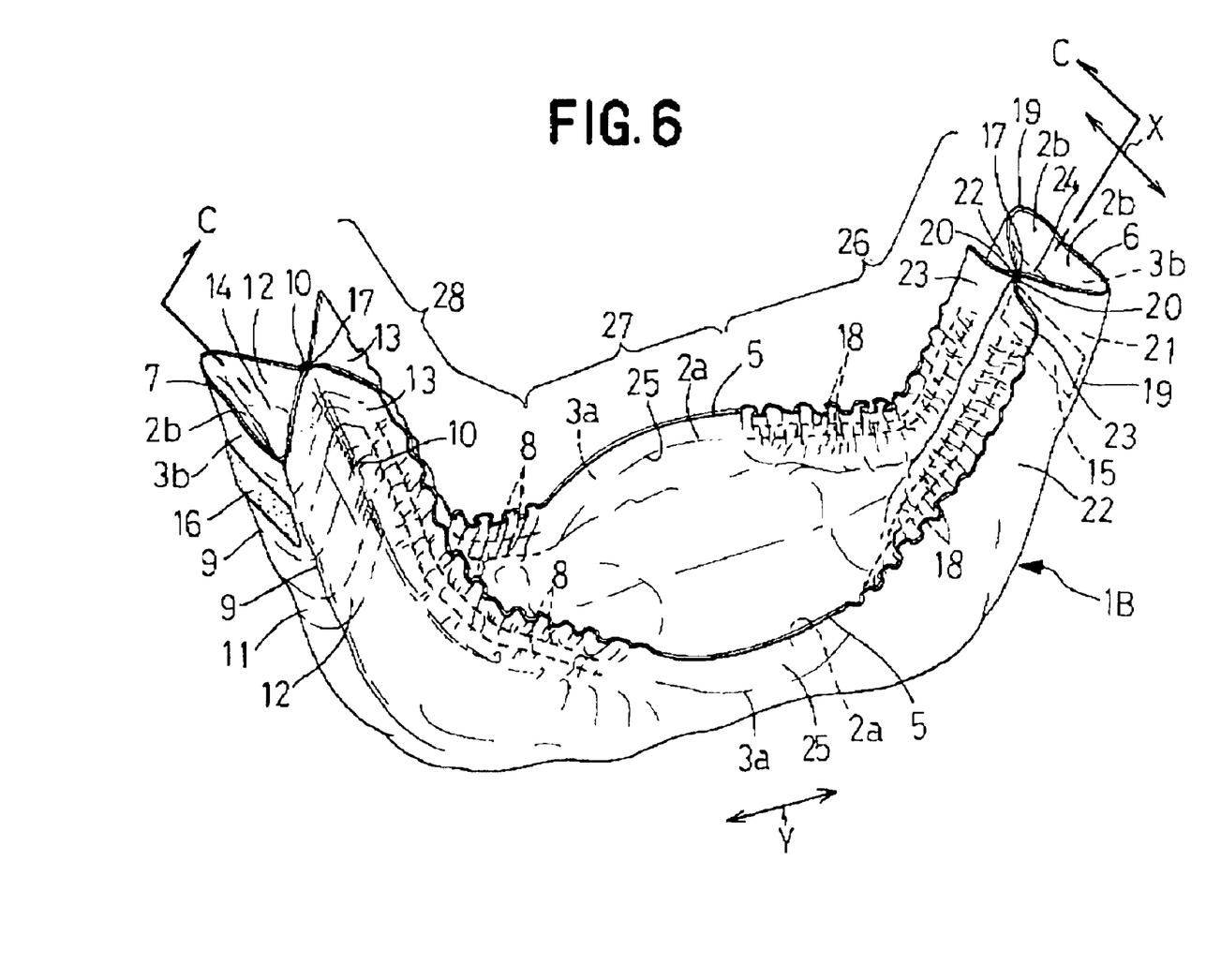
FIG. 6 is a perspective view showing another embodiment of the liquid-absorbent pad according to this invention.
Figure 7:
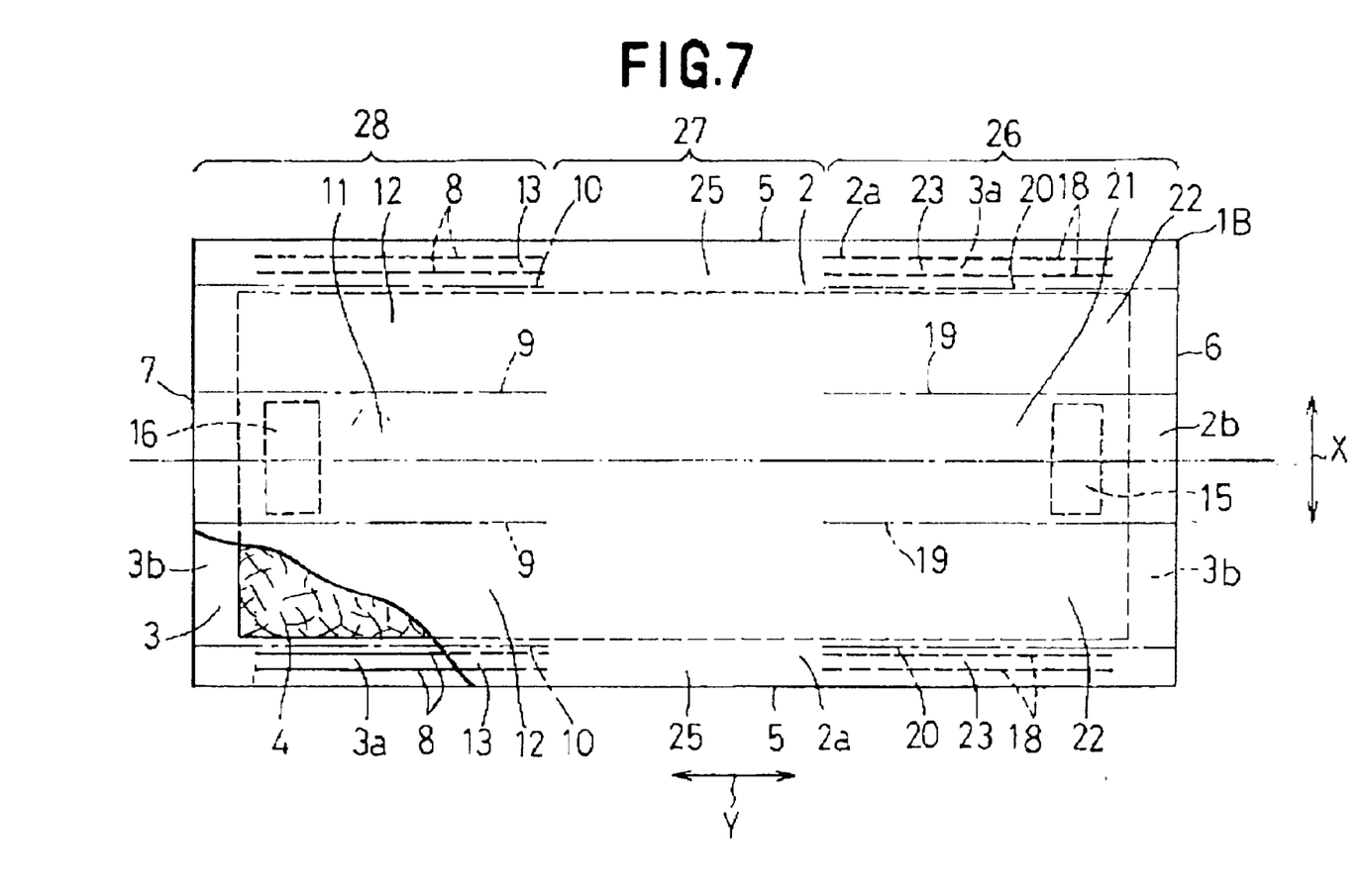
FIG. 7 is a partially cutaway plan view showing this pad before shaped into the pad.
Figure 8:
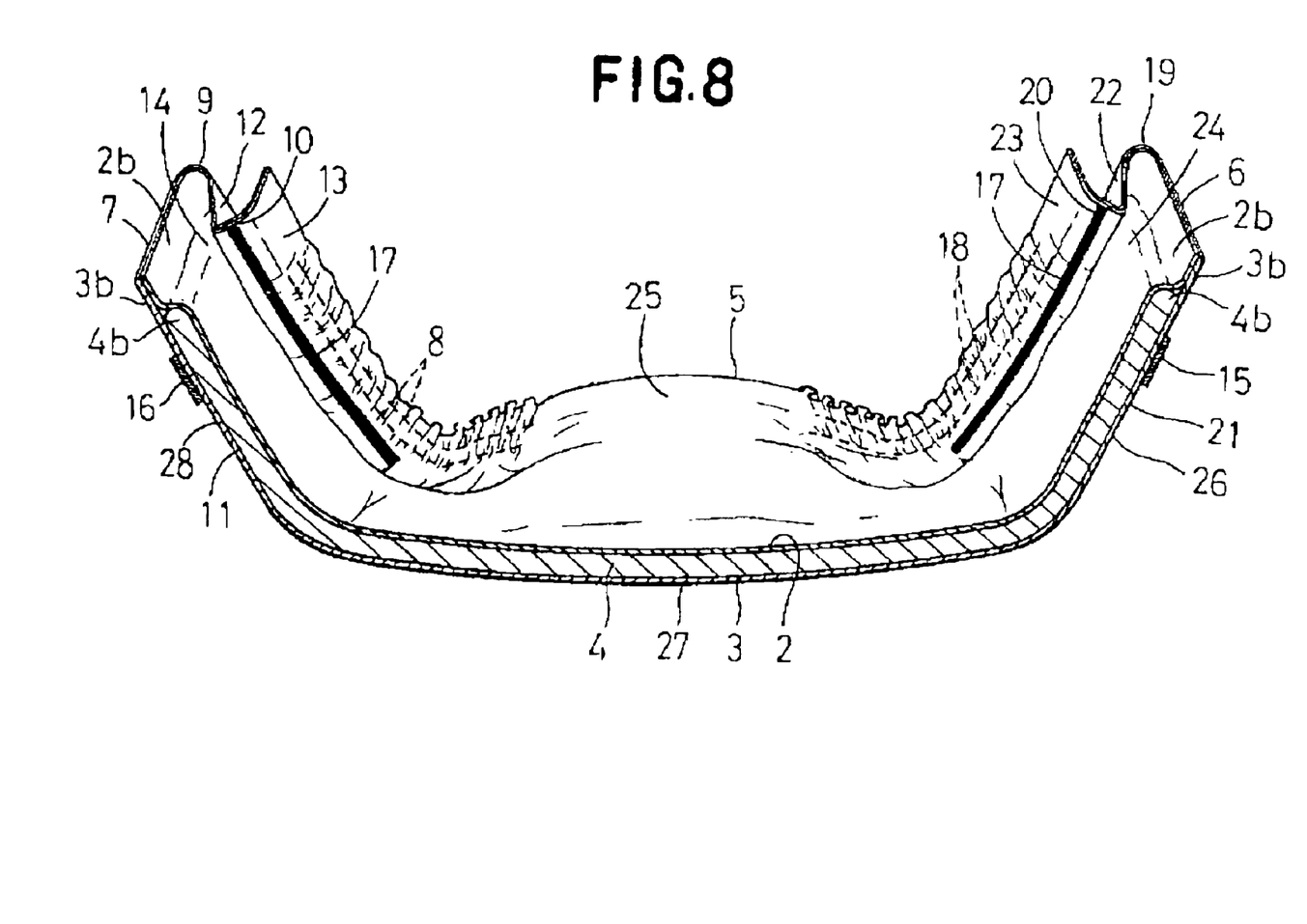
FIG. 8 is a cross-sectional view taken along a line C—C in FIG. 6.

FIG. 6 is a perspective view showing another embodiment 1B of the liquid-absorbent pad according to this invention, FIG. 7 is a partially cutaway plan view showing the pad 1B before shaped into the pad 1B and FIG. 8 is a cross-sectional view taken along a line C—C in FIG. 6. In FIGS. 6 and 7, the transverse direction of the pad 1B is indicated by the arrow X and its longitudinal direction is indicated by the arrow Y. What distinguishes the pad 1B from the pad 1A of FIG. 1 will be described below.

In the front region 26, the pad 1B is provided, in the vicinity of the side edges 5, with a plurality of elastically stretchable members 18 extending in the longitudinal direction and bonded in a stretched state thereto. These elastic members 18 are interposed between the top- and backsheets 2, 3 and secured to the respective inner surfaces of these sheets 2, 3.

In the front region 26, the pad 1B is folded inwardly with the topsheet 2 inside to the transverse direction along a pair of inward folding lines 19 extending in the longitudinal direction on both sides of a longitudinal center line L. The front region 26 is further folded outwardly in the transverse direction along a pair of outward folding lines 20 (second folding lines) extending in the longitudinal direction between the respective inward folding lines 19 and the respectively adjacent side edges 5. In the vicinity of the side edges 5, the pad 1B is folded and overlaid along the outward folding lines 20 in the front region 26 and the outer surface of the topsheet 2 is joined together along these outward folding lines 20 by means of hot melt adhesive 17.

The pad 1B folded in this manner in the front region 26 defines a bottom wall 21 extending between the inward folding lines 19, opposite side walls 22 extending between the respective inward folding lines 19 and the respectively adjacent outward folding lines 20, and a pair of flanges 23 extending outwardly in the transverse direction from the respective outward folding lines 20 toward the respectively adjacent side edges 5. In this manner, the pad 1B defines in the front region 26 a penis receiving space 24 surrounded by the bottom wall 21 and the opposite side walls 22. The penis receiving space 24 has an apex defined by the front end 6 and uprises obliquely forward. In the intermediate region 27 extending in the vicinity of the side edges 5, a pair of barriers 25 are formed uprising substantially in a vertical direction to apices defined by the respective side edges 5. In the respective bottom walls 11, 21 of the front and rear regions 26, 28, the outer surface of the backsheet 3 is coated with adhesives 15, 16 protectively covered with release paper (not shown).

To obtain the pad 1B of FIG. 6 from a state shown in FIG. 7, the pad 1B in the rear region 28 is folded along the inward folding lines 19 with the topsheet 2 inside, then folded along the outward folding lines 20 and finally the outer surface of the topsheet 2 is joined together along the outward folding lines 20. The pad 1B is then folded in the front region 26 along the inward folding lines 19 with the topsheet 2 inside, then folded along the outward folding lines 20 and finally the outer surface of the topsheet 2 is joined together along the outward folding lines 20.

Figure 9:
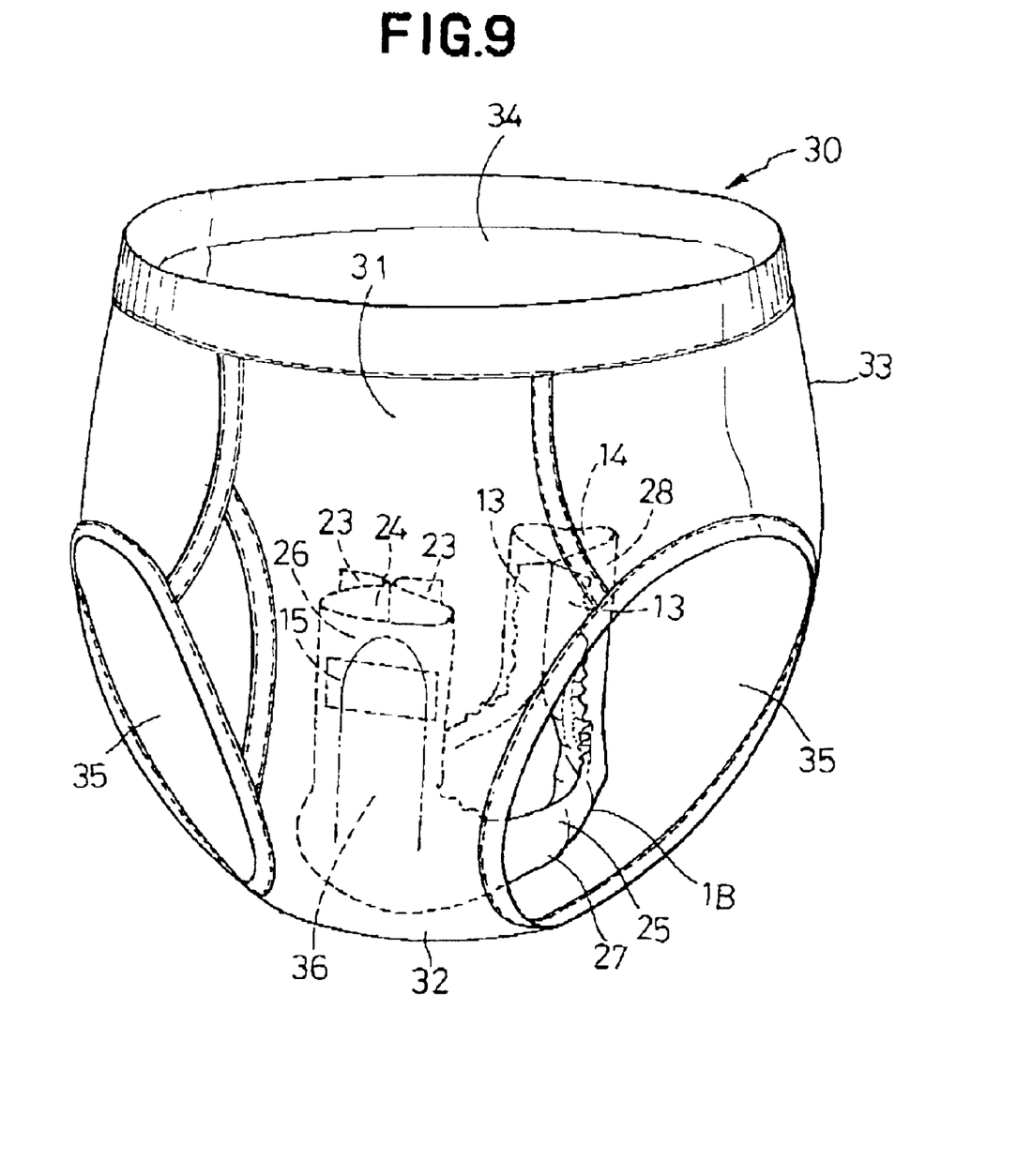
FIG. 9 is a perspective view showing the pad of FIG. 6 as attached to the inner side of the pants.

FIG. 9 is a perspective view showing the pad 1B of FIG. 6 as attached to the inner side of the pants 30. In the pad 1B, similarly to the pad 1A of FIG. 1, the outer surface of the backsheet 3 is fixed to the inner side of the pants 30 by means of adhesives 15, 16. The wearer wears the pants 30 with the pad 1B attached thereto so that his penis may be received by the penis receiving space 24 defined in the front region 26.

In the case of the pad 1B, the excretion receiving space 14 extends up- and rearward toward its apex defined by the rear end 7 and the penis receiving space 24 extends up and forward. Therefore it is unnecessary to bend the front and rear regions 26, 28 so as to follow the curvature of the pants 30 when the pad 1B is attached to the pants 30. This feature facilitates the pad 1B to be attached to the pants 30.

In the case of the pad 1B, the penis receiving space 24 can reliably absorb and retain urine. In this way, there is unlikely that any amount of urine might leak from the side edges 5 and from the front end 6 in the front region 26 of the pad 1B. In the intermediate region 27 extending in the vicinity at the side edges 5, barriers 25 are formed against excretion and these barriers 25 eliminate the anxiety that excretion might leak beyond the side edges 5 in the intermediate region 27. As the pad 1B comes in contact with the wearer's belly through the flanges 23 protecting the wearer from experiencing an uncomfortable stimulation by the side edges 5 which otherwise might directly contact the wearer's belly.

In the pad 1B, the elastic members 18 attached to the pad 1B in the front region 26 in the vicinity of the side edges 5 facilitate the penis receiving space 24 to uprise. It is not essential to provide the pad 1B with the elastic members 18 in the vicinity of the side edges 5 in the front region 26. Alternatively, this pad 1B may be provided in the vicinity of the side edges 5 of the front and rear regions 26, 28 as well as of the intermediate region 27 with elastic members bonded in a stretched state thereto.

The topsheet 2 may be made of a hydrophilic fibrous nonwoven fabric or finely porous plastic film. The backsheet 3 may be made of a hydrophobic fibrous nonwoven fabric, liquid-impervious plastic film, two-layers of hydrophobic nonwoven fabric overlaid each other or a composite sheet with a plastic film bonded to hydrophobic fibrous nonwoven fabric.

It is also possible to make the backsheet 3 using a composite nonwoven fabric with a highly water-resistant nonwoven fabric by melt blown method sandwiched by a nonwoven fabric with high strength and flexibility by spun-bond method.

Nonwoven fabric used herein may be selected from a group of materials including those obtained by spun lace-, needle punch-, melt blown-, thermal bond-, spun bond-, chemical bond and air through-processes. Component fibers of such nonwoven fabric may be selected from a group of materials consisting of polyolefine-, polyester- and polyamide-based fibers and core-sheath type or side-by-side type conjugated fiber of polyethylene/polypropylene or polyethylene/polyester.

The core 4 comprises a mixture of fluff pulp and super-absorbent polymer particles or a mixture of fluff pulp, super-absorbent polymer particles and thermoplastic synthetic resin fiber, in both cases, compressed to a desired thickness. Preferably, the core 4 is entirely covered with tissue paper and joined to this tissue paper in order to prevent the core 4 from losing its shape and to prevent the polymer particles from falling off. As the polymer particles, starch-, cellulose- or synthetic polymer-based particles may be used.

Bonding of the top- and backsheets 2, 3, fixing of the core 4 and attachment of the elastic members 8, 18 may be carried out using hot melt adhesive or welding technique such as heat-sealing or ultrasonic sealing.

The pads 1A, 1B illustrated as the typical embodiments of this invention may be attached in actual uses not only to the pants 30 but also to the inner surface of an open-type diaper cover. When these pads are used with the diaper cover, the pads 1A, 1B may be attached to the inner side of the diaper cover and then the front and rear waist regions of the diaper cover may be connected immediately before worn.

The disposable liquid-absorbent pad according to this invention is adapted to receive excretion discharged thereon in the excretion receiving space defined in the rear region of the pad and thereby to eliminate the anxiety that excretion might leak beyond the side edges as well as the rear end in the rear region of the pad. In this pad, the flanges formed in its rear region come in contact with the wearer's hip and protect the wearer from experiencing an uncomfortable stimulation by the side edges which otherwise might directly contact with the wearer's hip.

In the embodiment of the pad which defines not only the excretion receiving space but also the penis receiving space in the front region of the pad, urine discharged on the pad can be reliably absorbed and retained by this penis receiving space and therefore it is not apprehended that any amount of urine discharged on the pad might leak beyond side edges and the front edge in the front region of the pad. Portions of the intermediate region extending in the vicinity of the side edges define the barriers against excretion and these barriers eliminate the anxiety that excretion might leak beyond the side edges in the intermediate region. The flanges formed in the front region come in contact with the wearer's belly and protect the wearer from experiencing an uncomfortable irritation by the side edges which otherwise might directly contact the wearer's belly.

What is claimed is:

1. A disposable liquid-absorbent pad which is relatively long in dimension in a wearer's front and rear direction, comprising:

a liquid-pervious topsheet facing a wearer's skin;

a liquid-impervious backsheet facing away from the wearer's skin;

a liquid-absorbent core interposed between;

said pad having, in a longitudinal direction, of a front region, a rear region and an intermediate region extending between these front and rear regions wherein said pad is contoured by transversely opposite side edges extending in said longitudinal direction, a front end extending in said front region in a transverse direction and a rear end extending in said rear region in said transverse direction;

said pad being folded inwardly in said rear region in a vicinity of transversely apposite side edges with said topsheet inside, further folded outwardly in a transverse direction along a pair of first folding lines extending inside said side edges in said longitudinal direction and joined together along said first folding lines;

said pad defining in said rear region an excretion receiving space extending up- and rearward to said rear end defining an apex and a pair of flanges extending outwardly from said folding lines to said side edges in said transverse direction;

said pad is in said front region folded inwardly with said topsheet inside in the vicinity of transversely opposite side edges, then folded outwardly in said transverse direction along a pair of second folding lines extending inside said side edges, respectively, in said longitudinal direction and finally bonded together along said second folding lines; and said pad defines in said front region a penis receiving space extending upward and forward to said front end defining an apex and a pair of flanges extending outwardly from said folding lines to said side edges, respectively, in said transverse direction and said intermediate region defines, in the vicinity of said side edges, a pair of barriers extending up ward to apices defined by said side edges.

2. The pad according to claim 1, wherein said pad is in said rear region provided in the vicinity of said side edges with elastically stretchable members extending in said longitudinal direction bonded thereto in a stretched state.

3. The pad according to claim 1, wherein said elastically stretchable members extending in said longitudinal direction are bonded in a stretched state to said front region and said intermediate region, at least to said front region, in the vicinity of said side edges.

* * * * *